US009176487B2

(12) United States Patent
Sperling et al.

(10) Patent No.: US 9,176,487 B2
(45) Date of Patent: Nov. 3, 2015

(54) METHODS AND MATERIALS FOR REDUCING THE RISK OF INFECTIONS

(71) Applicant: Mayo Foundation for Medical Education and Research, Rochester, MN (US)

(72) Inventors: John W. Sperling, Rochester, MN (US); Adam A. Sassoon, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 88 days.

(21) Appl. No.: 13/659,607

(22) Filed: Oct. 24, 2012

(65) Prior Publication Data

US 2013/0101653 A1  Apr. 25, 2013

Related U.S. Application Data

(60) Provisional application No. 61/550,795, filed on Oct. 24, 2011.

(51) Int. Cl.

| | | |
|---|---|---|
| *A61B 19/08* | (2006.01) | |
| *A61B 17/00* | (2006.01) | |
| *G05B 15/02* | (2006.01) | |
| *A61K 31/7048* | (2006.01) | |
| *A61K 31/7056* | (2006.01) | |
| *A61L 31/16* | (2006.01) | |
| *H04L 12/26* | (2006.01) | |
| *H04L 29/06* | (2006.01) | |

(52) U.S. Cl.
CPC ............... *G05B 15/02* (2013.01); *A61B 19/08* (2013.01); *A61K 31/7048* (2013.01); *A61K 31/7056* (2013.01); *A61L 31/16* (2013.01); *H04L 43/08* (2013.01); *H04L 63/1433* (2013.01); *A61B 19/088* (2013.01); *A61B 2017/00889* (2013.01); *A61L 2300/404* (2013.01)

(58) Field of Classification Search
CPC .. A61B 19/08; A61B 19/088; A61B 31/7048; A61B 2017/00889; A61L 2300/404
See application file for complete search history.

(56) References Cited

U.S. PATENT DOCUMENTS

| | | | |
|---|---|---|---|
| 6,502,699 B1* | 1/2003 | Watson | 206/571 |
| 6,910,822 B2 | 6/2005 | Hidle et al. | |
| 7,066,908 B2* | 6/2006 | Kuracina et al. | 604/116 |
| 2010/0299796 A1 | 12/2010 | Hashemian | |
| 2011/0105976 A1 | 5/2011 | Berlin | |
| 2012/0222686 A1* | 9/2012 | Lockwood et al. | 128/849 |

OTHER PUBLICATIONS

Mangram, A., et al. "Guideline for prevention of surgical site infection", 1999, AJIC, 27:97-134.*

3M, "3M™ DuraPrep™ Surgical Solution (Iodine Povacrylex [0.7% available Iodine] and Isopropyl Alcohol, 74% w/w) Patient Preoperative Skin Preparation," 3M [online] [retrieved on Jul. 8, 2009] Retrieved from the Internet: < URL: http://products3.3m.com/catalog/us/en001/healthealt/professional/node_GSF83Z3YYXbe/rootrootCG4S9T . . . >, 2 pages.

3M, "Not all antimicrobial incise drapes are created equal," copyright 2004/2007, 2 pages.

Athwal et al., "Acute deep infection after surgical fixation of proximal humeral fractures," *J Shoulder Elbow Surg.*, 16(4):408-412, Epub Apr. 2007.

Athwal et al., "Deep infection after rotator cuff repair," *J Shoulder Elbow Surg.*, 16(3):306-311, Epub Feb. 2007.

Butler-Wu et al., "Optimization of periprosthetic culture for diagnosis of Propionibacterium acnes prosthetic joint infection," *J Clin Microbiol.* 49(7):2490-2495, Epub May 2011.

Cheung et al., "Infection associated with hematoma formation after shoulder arthroplasty," *Clin Orthop Relat Res.*, 466(6):1363-1367, Epub Apr. 2008.

Cove and Holland, "The effect of benzoyl peroxide on cutaneous micro-organisms in vitro," *J Appl Bacteriol.*, 54(3):379-382, Jun. 1983.

Duncan and Sperling, "Treatment of primary isolated shoulder sepsis in the adult patient," *Clin Orthop Relat Res.*, 466(6):1392-1396, print Jun. 2008, Epub Mar. 2008.

Duncan et al., "Infection after clavicle fractures," *Clin Orthop Relat Res.*, 439:74-78, Oct. 2005

Haidukewych and Sperling, "Results of treatment of infected humeral nonunions: the Mayo Clinic experience," *Clin Orthop Relat Res.*, (414):25-30, Sep. 2003.

Kelly and Hobgood, "Positive culture rate in revision shoulder arthroplasty," *Clin Orthop Relat Res.*, 467(9):2343-2348, Epub May 2009.

Levy et al., "Propionibacterium acnes postoperative shoulder arthritis: an emerging clinical entity," *Clin Infect Dis.* 46(12):1884-1886, Jun. 2008.

Mileti et al., "Reimplantation of a shoulder arthroplasty after a previous infected arthroplasty," *J Shoulder Elbow Surg.*, 13(5):528-531, Sep.-Oct. 2004.

Mileti et al., "Shoulder arthroplasty for the treatment of postinfectious glenohumeral arthritis," *J Bone Joint Surg Am.*, 85-A(4):609-614, Apr. 2003.

Murray et al., "Efficacy of preoperative home use of 2% chlorhexidine gluconate cloth before shoulder surgery," *J Shoulder Elbow Surg.*, 20(6):928-933, Epub May 2011.

Patel et al., "Propionibacterium acnes colonization of the human shoulder," *J Shoulder Elbow Surg.*, 18(6):897-902, print Nov.-Dec. 2009, Epub Apr. 2009.

Piper et al., "Microbiologic diagnosis of prosthetic shoulder infection by use of implant sonication," *J Clin Microbiol.*, 47(6):1878-1884, Epub Mar. 2009.

(Continued)

*Primary Examiner* — Gina Justice
(74) *Attorney, Agent, or Firm* — Fish & Richardson P.C.

(57) ABSTRACT

This document relates to methods and materials for reducing the risk of infection after a shoulder surgery or medical procedure. For example, this document relates to methods and materials for using a topical composition containing clindamycin or erythromycin to reduce the risk of or to prevent infection associated with shoulder surgeries or medical procedures.

6 Claims, 3 Drawing Sheets

(56) References Cited

OTHER PUBLICATIONS

Saltzman et al., "Efficacy of surgical preparation solutions in shoulder surgery," *J Bone Joint Surg Am.*, 91(8):1949-1953, Aug. 2009.

Sperling et al., "Infection after shoulder arthroplasty," *Clin Orthop Relat Res.*, (382):206-216, Jan. 2001.

Sperling et al., "Infection after shoulder instability surgery," *Clin Orthop Relat Res.* (414):61-64, Sep. 2003

Strickland et al., "The results of two-stage re-implantation for infected shoulder replacement," *J Bone Joint Surg Br.*, 90(4):460-465, Apr. 2008.

Topolski et al., "Revision shoulder arthroplasty with positive intraoperative cultures: the value of preoperative studies and intraoperative histology," *J Shoulder Elbow Surg.*, 15(4):402-406, Jul.-Aug. 2006.

* cited by examiner

METHODS AND MATERIALS FOR REDUCING THE RISK OF INFECTIONS

CROSS-REFERENCE TO RELATED APPLICATIONS

This application claims the benefit of U.S. Provisional Application Ser. No. 61/550,765, filed Oct. 24, 2011. The disclosure of the prior application is considered part of (and is incorporated by reference in) the disclosure of this application.

BACKGROUND

1. Technical Field

This document relates to methods and materials for reducing the risk of infection after a surgery (e.g., a shoulder surgery or medical procedure). For example, this document relates to methods and materials for using a topical antibacterial composition containing clindamycin or erythromycin to reduce the risk of or prevent infections associated with shoulder medical procedures. In some cases, topical administration of a topical composition containing clindamycin or erythromycin can be carried out before, during, and after surgery.

2. Background Information

*Propionibacterium acnes* has become recognized as the primary organism responsible for infection after shoulder surgery. This has been documented in multiple studies of infection after rotator cuff surgery, shoulder replacement surgery, instability surgery of the shoulder, clavicle fractures, proximal humerus fractures, and mid-shaft humerus fractures. Additionally, studies have shown that *Prop. acnes* is essentially nonexistent in native shoulder sepsis. Currently, DuraPrep™ Surgical Solution (3M) or ChloraPrep® Solution (CareFusion) is used to prepare the arm for surgery. Following skin preparation, the operative region is then wrapped in a 3M Ioban™ drape.

SUMMARY

This document provides methods and materials for reducing the risk of or preventing post-operative infection (e.g., post-operative shoulder surgery infection). In some cases, it is possible that *Prop. acnes* can be introduced into a shoulder wound at the time of surgery, and despite the use of skin preparation solutions and barrier drapes, a significant problem of bacteria contamination may exist. The methods and materials provided herein can be used to reduce the risk of or to prevent post-operative infection (e.g., post-operative shoulder surgery infection such as a post-operative shoulder surgery *Prop. acnes* infections). As described herein, topical administration of an antibacterial composition pre-, intra-, and post-operatively can be used to reduce the risk of or to prevent post-operative shoulder surgery infection (e.g., post-operative shoulder surgery *Prop. acnes* infections). In some cases, such an antibacterial composition can include clindamycin, erythromycin, or a combination of clindamycin and erythromycin.

In general, one aspect of this document features a method for reducing risk of post-operative infection. The method comprises, or consist essentially of, (a) applying a first topical antibacterial composition to at least a portion of an operative site before an operative intervention, and (b) applying a second topical antibacterial composition to at least a portion of the operative site immediately before the operative intervention, wherein the first and second topical antibacterial compositions comprise clindamycin, erythromycin, or a combination thereof The operative intervention can be a shoulder injection. The operative intervention can be a shoulder surgery. The shoulder surgery can be selected from the group consisting of rotator cuff surgery, shoulder replacement surgery, instability surgery of the shoulder, clavicle fracture surgery, proximal humerus fracture surgery, and mid-shaft humerus fracture surgery.

The first topical antibacterial composition can be applied multiple times before the surgical intervention. The first topical antibacterial composition can be applied using a deodorant applicator. The first topical antibacterial composition can be applied by wiping the skin with a wipe impregnated with the first topical antibacterial composition. The method can further comprise dressing the surgical site post-operatively with dressings that are impregnated with a third topical antibacterial composition comprising clindamycin. The first, second, or third topical antibacterial composition can further comprise clindamycin or erythromycin and a second antibiotic.

In another aspect, this document features a surgical drape for preventing post-operative infection. The drape can be impregnated with a topical antibacterial composition comprising clindamycin, erythromycin, or a combination thereof In another aspect, this document features a method for reducing risk of post-operative infection. The method comprises, or consists essentially of, (a) instructing a patient to apply a first topical antibacterial composition to at least a portion of an operative site before an operative intervention, (b) intra-operatively applying a second topical antibacterial composition to at least a portion of the operative site, and (c) instructing the patient to apply a third topical antibacterial composition to at least a portion of the operative site after the operative intervention, wherein the first, second, and third topical antibacterial compositions comprise clindamycin, erythromycin, or a combination thereof.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

This document provides methods and materials for reducing the risk of or preventing post-operative infection (e.g., post-operative shoulder surgery infection). For example, this document provides methods and materials for using a composition containing clindamycin, erythromycin, or a combination thereof to reduce the risk of or to prevent infection following a shoulder surgery or medical procedure.

The methods and materials provided herein can be used to reduce the risk of or prevent infections after any type of surgery. For example, the methods and materials provided herein can be used to reduce the risk of or prevent post-operative infection following shoulder surgery, cardiac and thoracic surgery, abdominal and pelvic surgery, head and neck surgery, hip and knee surgery, elbow, hand, and/or wrist surgery, spine surgery, neurosurgery, or foot and/or ankle surgery.

Examples of shoulder surgeries and medical procedures include, without limitation, rotator cuff surgery, shoulder replacement surgery, instability surgery of the shoulder, clavicle fracture surgery, proximal humerus fracture surgery, mid-shaft humerus fracture surgery, acromioplasty, distal clavicle excision, arthroscopic debridement, labral repair, a shoulder steroid injections, a shoulder anesthetic injections, or a shoulder visco-supplementation injection.

Figure 1:
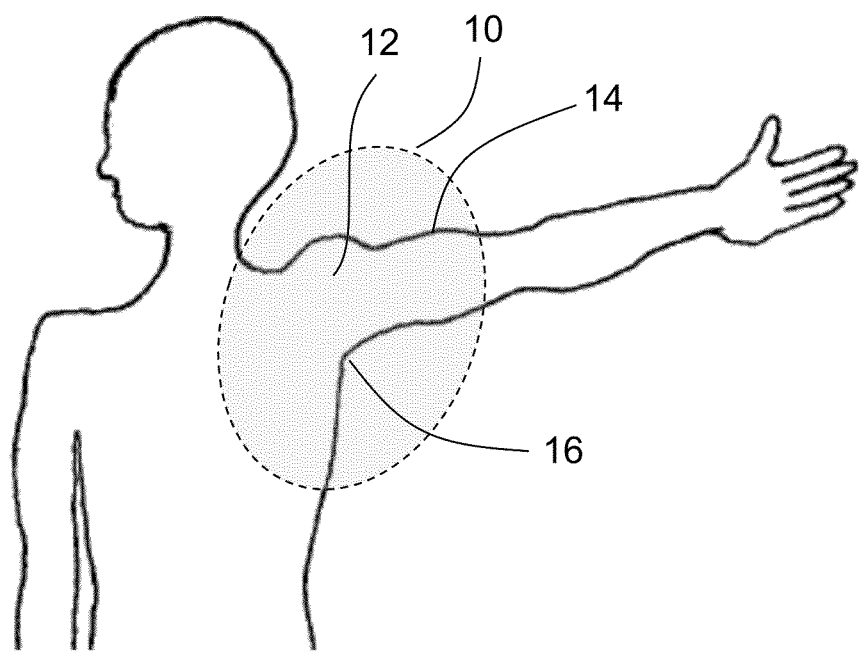
FIG. 1 is a perspective view of a patient's torso with an arm extended in a traditional shoulder surgery position.

The operative site of a surgery (e.g., a shoulder surgery or medical procedure) refers to that skin surface area that needs to be covered by a surgical drape during the surgery (e.g., during the shoulder surgery or medical procedure). In some cases, a general area of an operative site 10 for a shoulder surgery is shown in FIG. 1. This area includes the shoulder 12, upper portion of the arm 14, and axilla 16. In some cases, a surgeon can give instructions to the patient undergoing a shoulder surgery or medical procedure exactly what areas are included in the surgical site based upon the surgery or procedure being performed.

As described herein, an antibacterial composition can be topically applied to at least a portion of the operative site of the patient before, during, and after the surgery or procedure. An antibacterial composition provided herein can include clindamycin, erythromycin, or combinations thereof. The particular antibacterial composition used for the pre-, intra-, and post-operative application can be the same composition (e.g., a clindamycin composition for each application) or can be different (e.g., a clindamycin composition for the pre- and intra-operative application and an erythromycin composition for the post-operative application). When using clindamycin, the clindamycin in the composition can be a pharmaceutical grade salt or ester of clindamycin. Pharmaceutically acceptable salts, esters, or solvates of clindamycin refer to those that possess the desired pharmacological activity and which are neither biologically nor otherwise undesirable. The salts, esters, or solvates can be formed with inorganic or organic acids such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate, heptanoate, hexanoate, hydrochloride, hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate, and undecanoate.

In some cases, base salts, esters, or solvates including, without limitation, ammonium salts, alkali metal salts such as lithium, sodium and potassium salts, alkaline earth metal salts such as calcium and magnesium salts, salt with organic bases such as dicyclohexylamine salts, N-methyl-D-glucamine, and salts with amino acids such as arginine, lysine, and so forth can be used as described herein. In some cases, base salts, esters, or solvates can include basic nitrogen-containing groups. Such basic nitrogen-containing groups can be quarternized with agents such as (1) lower alkyl halides such as methyl, ethyl, propyl, and butyl chloride, bromides and iodides, (2) dialkyl sulfates such as dimethyl, diethyl, dibutyl and diamyl sulfates, (3) long chain alkyls such as decyl, lauryl, myristyl and stearyl substituted with one or more halide such as chloride, bromide, and iodide, and (4) aryl or arylalkyl halides such as benzyl and phenethyl bromide and others.

In some cases, clindamycin phosphate (ester) or clindamycin hydrochloride (salt) can be used as described herein as pharmaceutically acceptable esters or salts of clindamycin due to their compatibility with gelling agents and extensive history of topical use.

Since erythromycin can be limited in its solubility, dermatologic solvents such as alcohol or acetone can be used. In solution, erythromycin can rapidly degrade, even at normal room temperature. Refrigeration can be used to somewhat extend the shelf life of such solutions. In some cases, an erythromycin derivative or analogue can be used as described herein.

In some cases, a particular antimicrobial composition or combination of antimicrobial compositions can be used to reduce the risk of or to prevent post-operative infection following a particular surgery. For example, the antimicrobial compositions or combinations of antimicrobial compositions set forth in Table 1 can be used to reduce the risk of or to prevent post-operative infection following a particular surgery as set forth in Table 1.

TABLE 1

Antimicrobial agents for reducing the risk of or for preventing infection following surgery.

| Surgery Type | Operative Site | Microbial Organisms | Antimicrobial Agents |
| --- | --- | --- | --- |
| Shoulder | Shoulder | *Prop. acnes* | Clindamycin, erythromycin, or a combination thereof |
| Hip | Hip | *Staphylococcus aureus* and/or *Staphylococcus epidermidis* | Mupirocin, retapamulin, or a combination thereof |
| Knee | Knee | *Staphylococcus aureus* and/or *Staphylococcus epidermidis* | Mupirocin, retapamulin, or a combination thereof |
| Cardiac | Cardiac | *Staphylococcus aureus* and/or *Staphylococcus epidermidis* | Mupirocin, retapamulin, or a combination thereof |
| Spine | Spine | *Staphylococcus epidermidis* and/or *Propionibacterium acnes* | Mupirocin, retapamulin, clindamycin, erythromycin, or a combination thereof |

TABLE 1-continued

Antimicrobial agents for reducing the risk of
or for preventing infection following surgery.

| Surgery Type | Operative Site | Microbial Organisms | Antimicrobial Agents |
|---|---|---|---|
| Neurosurgery | Spine and Skull | *Staphylococcus aureus*, *Staphylococcus epidermidis*, and/or *Propionibacterium acnes* | Mupirocin, retapamulin clindamycin, erythromycin, or a combination thereof |

A composition provided herein for reducing the risk of or preventing post-operative infection (e.g., post-operative shoulder infection) can included any appropriate concentration of an antimicrobial or antibacterial agent (e.g., clindamycin and/or erythromycin) that effectively kills or reduces replication of microbes or bacteria (e.g., *Prop. Acnes*). For example, a composition designed for topical administration can include from about 0.1% to about 5% by weight of clindamycin and/or erythromycin.

In some cases, a topical antimicrobial or antibacterial composition can include one or more antimicrobial or antibacterial agents. For example, an antibacterial composition provided herein can include clindamycin and/or erythromycin in combination with any one or more of the following agents: azelaic acid, benzyol peroxide, sodium sulfacetamide, azithromycin, clarithromycin, lincomycin, and salts thereof. In some cases, a topical antimicrobial or antibacterial composition provided herein can include a retinoid such as adapalene, tazarotene, or tretinoin.

A topical composition provided herein may take the form of a gel, cream, lotion, suspension, emulsion, ointment, foam, or mixtures thereof Other cosmetic treatment compositions known to those skilled in the art, including liquids and balms can be designed to include an antimicrobial or antibacterial agent and used as described herein. In some cases, an antimicrobial or antibacterial composition provided herein can be applied with an applicator. Examples of applicators that can be used to apply an antimicrobial or antibacterial composition as described herein include, without limitation, pledgets and pads. In some cases, an antimicrobial or antibacterial composition may be incorporated into an adhesive patch or soap, or formulated such that it can be delivered with an applicator typically used to apply deodorant.

Emulsions, such as oil-in-water or water-in-oil systems, as well as a base (vehicle or carrier) for the topical formulation can be selected to provide effectiveness of the active ingredient and/or avoid allergic and irritating reactions (e.g., contact dermatitis) caused by ingredients of the base or by the active ingredients.

In some case, an antimicrobial or antibacterial composition to be used as described herein can include one or more emulsifiers. Examples of emulsifiers useful in this regard include, without limitation, glycol esters, fatty acids, fatty alcohols, fatty acid glycol esters, fatty esters, fatty ethers, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, tragacanth gum, poly(acrylamide-b-acrylic acid), 10-30 alkyl acrylate crosspolymers, derivatives thereof, and mixtures thereof Creams useful in the compositions used herein can be semisolid emulsions of oil and water. They can be easily applied and vanish when rubbed into the skin.

Lotions useful in the compositions used herein can include suspensions of powdered material in a water or alcohol base (e.g., calamine), as well as water-based emulsions (e.g., some corticosteroids).

Suitable lotions or creams containing the active compound may be suspended or dissolved in, for example, a mixture of one or more of the following mineral oil, sorbitan monostearate, polysorbate 60 (polyoxyethylene 20 sorbitan monostearate), cetyl ester wax, cetearyl alcohol, 2-octyldodecanol, benzyl alcohol, and water.

Suitable gelling agents which may be useful in the present compositions include aqueous gelling agents, such as neutral, anionic, and cationic polymers, and mixtures thereof Other suitable gelling agents include cellulosic polymers, such as gum arabic, gum tragacanth, locust bean gum, guar gum, xanthan gum, cellulose gum, methylcellulose, hydroxyethylcellulose, hydroxypropylcellulose, and hydroxypropylmethylcellulose.

Other, non-limiting example of suitable thickeners useful herein include cellulosic polymers, such as gum arabic, gum acacia, gum tragacanth, locust bean gum, guar gum, hydroxypropyl guar, xanthan gum, cellulose gum, sclerotium gum, carageenan gum, karaya gum, cellulose gum, rosin, methylcellulose, hydroxyethylcellulose, hydroxypropylcellulose, hydroxymethylcellulose, hydroxypropylmethylcellulose, methylhydroxyethylcellulose, cetyl hydroxyethylcellulose, carboxymethylcellulose, corn starch, hydroxypropyl starch phosphate, distarch phosphate, distarch dimethylene urea, aluminum starch octenyl succinate, maltodextrin, dextran, poly(acrylamide), PEG-150 distearate, PEG-150/decyl alcohol/SMDI copolymer, PEG-150/stearyl alcohol/SMDI copolymer, PEG-180/Laureth-50/TMMG copolymer, Polyether 1, acrylic acid/acrylamidomethyl propane sulfonic acid copolymer, acrylate/C10-30 alkyl acrylate crosspolymer, acrylate/beheneth-25 methacrylate copolymer, acrylate/steareth-20 methacrylate copolymer, acrylate/steareth-20 copolymer, acrylate/VA crosspolymer, acrylic acid/acrylonitrogen copolymer, ammonium acryloyldimethyltaurate/beheneth-25 methacrylate copolymer, ammonium acryloyldimethyltaurate/VP copolymer, caprylic/capric triglyceride (and) sodium acrylate copolymer, PVM/MA decadiene crosspolymer, alginic acid, propylene glycol alginate, dimethicone, silica dimethyl silylate, a dimethylacrylamide/acrylic acid/polystyrene ethyl methacrylate copolymer, derivatives thereof, and mixtures thereof Other common thickeners and/or gelling agents, such as polyacrylic polymers, may be further useful herein. These thickeners and/or gelling agents can be present in the instant compositions regardless of what form the final composition takes.

Any other non-toxic, inert, and effective carrier may be used to formulate an antimicrobial or antibacterial composition. Well-known carriers used to formulate other therapeutic compounds for administration to humans particularly will be useful in an antimicrobial or antibacterial composition. Pharmaceutically acceptable carriers, excipients and diluents in this regard are well known to those of skill in the art, such as those described in The Merck Index, Thirteenth Edition, Budavari et al., Eds., Merck & Co., Inc., Rahway, N.J. (2001). Examples of such useful pharmaceutically acceptable excipients, carriers, and diluents include distilled water, physiological saline, Ringer's solution, dextrose solution, Hank's solution, and DMSO.

These additional components, as well as effective formulations and administration procedures are well known in the art and are described in standard textbooks, such as Goodman and Gillman's: The Pharmacological Bases of Therapeutics, 8th Ed., Gilman et al. Eds. Pergamon Press (1990) and Remington's Pharmaceutical Sciences, 17th Ed., Mack Publishing Co., Easton, Pa. (1990).

Examples of excipients that can be used to formulate an antimicrobial or antibacterial composition include, without limitation, carbomers, polyacrylic polymers, glycerin, sodium hydroxide, sodium thiosulfate, propyl gallate, alkyl parabens, purified water, titanium dioxide, zinc oxide, and mixtures thereof.

Other ingredients which may optionally be provided in a topical composition include humectants, such as propylene glycol; solvents, such as alcohol (de minimis); sun filters, such as titanium dioxide, zinc oxide, and mixtures thereof; and anti-microbial preservatives, such as methylparaben and propylparaben. The topical compositions may also include an organic or inorganic base, such as sodium hydroxide, which is used to adjust the pH of the initial components and the final product.

In some cases, an antimicrobial or antibacterial composition designed to be used as described herein can additionally include remaining amounts of one or more dermatologically acceptable excipients. Examples of dermatologically acceptable excipients useful in these compositions include, without limitation, surfactants, preservatives, emollients, humectants, fluid alkyl alcohols, thickening agents, emulsifiers, suspending agents, pH modifiers/buffering agents, chelating agents, antioxidants, sun filters, derivatives thereof, and mixtures thereof Any appropriate surfactant, preservative, emollient, humectant, fluid alkyl alcohol, thickening agent, emulsifier, suspending agent, pH modifier, chelating agent, antioxidant, sun filter, or other dermatologically acceptable excipient commonly known to those of ordinary skill in the art as useful in topical compositions can be incorporated into an antimicrobial or antibacterial compositions provided herein. In some cases, any appropriate non-toxic, inert, and effective topical carrier may be used to formulate an antimicrobial or antibacterial composition described herein. Well-known carriers used to formulate other topical therapeutic compositions for administration to humans will be useful in these compositions. Examples of these components that are well known to those of skill in the art are described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide", U.S. Food and Drug Administration (FDA) Center for Drug Evaluation and Research (CDER) Office of Management, http://www.accessdata.fda.gov/scripts/cder/iig/index.cfm.

Pre-operative Application

The methods for reducing the risk of or preventing post-operative infection from a surgery (e.g., a shoulder surgery) or medical procedure can include a pre-operative application of a topical antimicrobial or antibacterial composition (e.g., a composition containing clindamycin, erythromycin, or a combination thereof). The antimicrobial or antibacterial composition for pre-operative application may take the form of a gel, cream, lotion, suspension, emulsion, ointment, foam, or a mixture or combination thereof In one embodiment, an antimicrobial or antibacterial composition is applied using an applicator that is typically used to apply an antiperspirant and that is in widespread use. For example, an antimicrobial or antibacterial composition can be in a semi-solid stick form where the composition is accommodated within a tube with one end of the stick exposed. The stick can be rubbed against the skin, thereby applying a small amount of the carrier material and antimicrobial or antibacterial composition. Another type of applicator can be a roller ball type in which the composition is received in liquid form in a container, the upper end of which affords a part-spherical seat in which a spherical applicator ball is rotatably received. If the container is inverted, and the applicator ball is rolled against the skin, the ball will rotate in its mounting, and a thin layer of an antimicrobial or antibacterial composition can be transferred from the interior of the container to the skin on the surface of the ball. Another type of applicator can be a pressurized aerosol can or container. An antimicrobial or antibacterial composition can be stored together with propellant in an aerosol can and can be sprayed as desired onto the skin.

In another embodiment, an antimicrobial or antibiotic composition can be applied using an adhesive transdermal patch such as those described in U.S. Patent Application Publication No. 2011/0105976 or 2010/0299796. The patch can be a single, large patch specifically configured to fit the arm and shoulder area, including the axilla. In some cases, multiple smaller patches can be used to cover the shoulder and axilla area.

In another embodiment, an antimicrobial or antibiotic composition can be formulated into a soap solution that can be used to wash the surgical site.

In another embodiment, an antimicrobial or antibiotic composition can be applied using disposable cloth wipes that are impregnated with the antimicrobial or antibiotic composition.

In another embodiment, the pre-operative application of an antimicrobial or antibacterial composition can include an additional combination therapy. The application of an antimicrobial or composition can be combined with a separate retinoid-containing source, such as for example topical tretinoin (retinoic acid) in 0.025%, 0.05%, or 0.1% cream, 0.05% liquid, or 0.01% or 0.025% gel. In some cases, another topical retinoid, Differin® brand adapalene 0.1% gel (Galderma Laboratories, San Antonio, Tex.), can be used since it may be slightly less irritating than topical tretinoin. Other retinoids, which can be used as an additional retinoid source in combination therapy, include Panretin®, containing alitretinoin, and Targretin®, containing bexarotene.

The patient undergoing a surgery (e.g., a shoulder surgery) or medical procedure can be given instructions to apply the pre-operative antimicrobial or antibacterial composition one time before the surgery or medical procedure or multiple times before the surgery or medical procedure. For example, a patient can be instructed to apply an antimicrobial or antibacterial composition the night before the surgery or medical procedure. In some cases, a patient can be instructed to apply an antimicrobial or antibacterial composition daily (or multiple times daily) for one, two, three, four, five, six, seven, eight, nine, ten, or more days prior to the surgery or medical procedure. In some cases, a patient can be instructed to apply an antimicrobial or antibacterial composition daily (or multiple times daily) for between one and 14 days prior to the surgery or medical procedure. The multiple times daily can be two, three, four, five, or more times daily.

Intra-Operative Application

The methods for reducing the risk of or preventing post-operative infection from a surgery (e.g., a shoulder surgery) or medical procedure can include an intra-operative application of a topical antimicrobial or antibacterial composition (e.g., a composition containing clindamycin, erythromycin, or a combination thereof). The term "intra-operative" as used herein refers to the time from when the patient is admitted to the clinical facility (e.g., a clinic or hospital) or clinical unit (e.g., surgery unit) for performance of the surgery or medical procedure to the time when the surgery or medical procedure is completed. The antimicrobial or antibacterial composition for intra-operative application may take the form of a gel, cream, lotion, suspension, emulsion, ointment, foam, or a mixture or combination thereof In some cases, the intra-operative antimicrobial or antibacterial composition can be in the form of a liquid. The antimicrobial or antibacterial composition can be applied using a cotton swab or an applicator such as the one described in U.S. Pat. No. 6,910,822. In some cases, an antibacterial composition containing clindamycin can be applied alone or in combination with DuraPrep™ Surgical Solution (3M), ChloraPrep® Solution (CareFusion), or Betadine (Purdue Frederick Co).

The intra-operative application of an antimicrobial or antibacterial composition can include using a surgical drape impregnated with the antimicrobial or antibacterial composition. For example, the drape can be the Ioban drape made by 3M Healthcare.

Post-Operative Application

The methods for reducing the risk of or preventing post-operative infection from a surgery (e.g., a shoulder surgery) or medical procedure can include a post-operative application of a topical antimicrobial or antibacterial composition (e.g., a composition containing clindamycin, erythromycin, or a combination thereof). The antimicrobial or antibacterial composition for intra-operative application may take the form of a gel, cream, lotion, suspension, emulsion, ointment, foam, or a mixture or combination thereof The post-operative antimicrobial or antibacterial composition can be applied by impregnating the dressings used to cover the surgical wounds with the antimicrobial or antibacterial composition. For example, an antimicrobial or antibacterial composition could be used in combination with a Mepilex® Border dressing (Mölnlycke® Health Care, Norcross, Georgia). In some cases, the post-operative antimicrobial or antibacterial composition can include the pre-operative antimicrobial or antibacterial compositions described above. The post-operative antimicrobial or antibacterial composition can be first applied or re-applied by the patient when the surgical wound dressings are changed or after they have been removed. The post-operative antimicrobial or antibacterial composition can be applied immediately following the surgery or medical procedure, one day following the surgery or medical procedure, or up to two weeks following the surgery or medical procedure.

Figure 2:
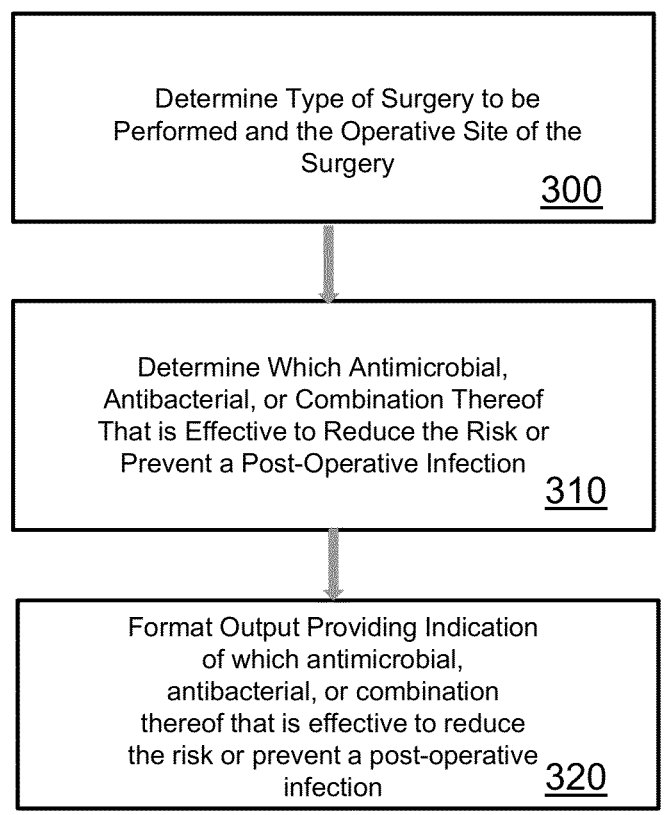
FIG. 2 is a flow chart of an exemplary process by which particular antimicrobial or antibacterial compositions or particular combinations of antimicrobial or antibacterial compositions for reducing the risk of or preventing a post-operative infection can be selected.

FIG. 2 shows an exemplary process by which particular antimicrobial or antibacterial compositions or particular combinations of antimicrobial or antibacterial compositions for reducing the risk of or preventing a post-operative infection can be selected. The process begins at box 300, where information regarding the type of surgery to be performed and the operative site of the surgery is collected. For example, a surgeon can provide information about the particular type of surgery to be performed and information about the particular location of the operative site of the surgery. At box 310, data regarding antimicrobial or antibacterial compositions or combinations of antimicrobial or antibacterial compositions effective for reducing the risk of or preventing a post-operative infection for the type of surgery to be performed and the operative site (e.g., data within a database) are assessed to determine possible antimicrobial or antibacterial compositions or combinations of antimicrobial or antibacterial compositions for the patient. At box 320, output providing an indication of possible antimicrobial or antibacterial compositions or possible combinations of antimicrobial or antibacterial compositions for the patient is formatted. Once formatted, the output can be presented to a user (e.g., a surgeon, clinician, or medical professional).

Figure 3:
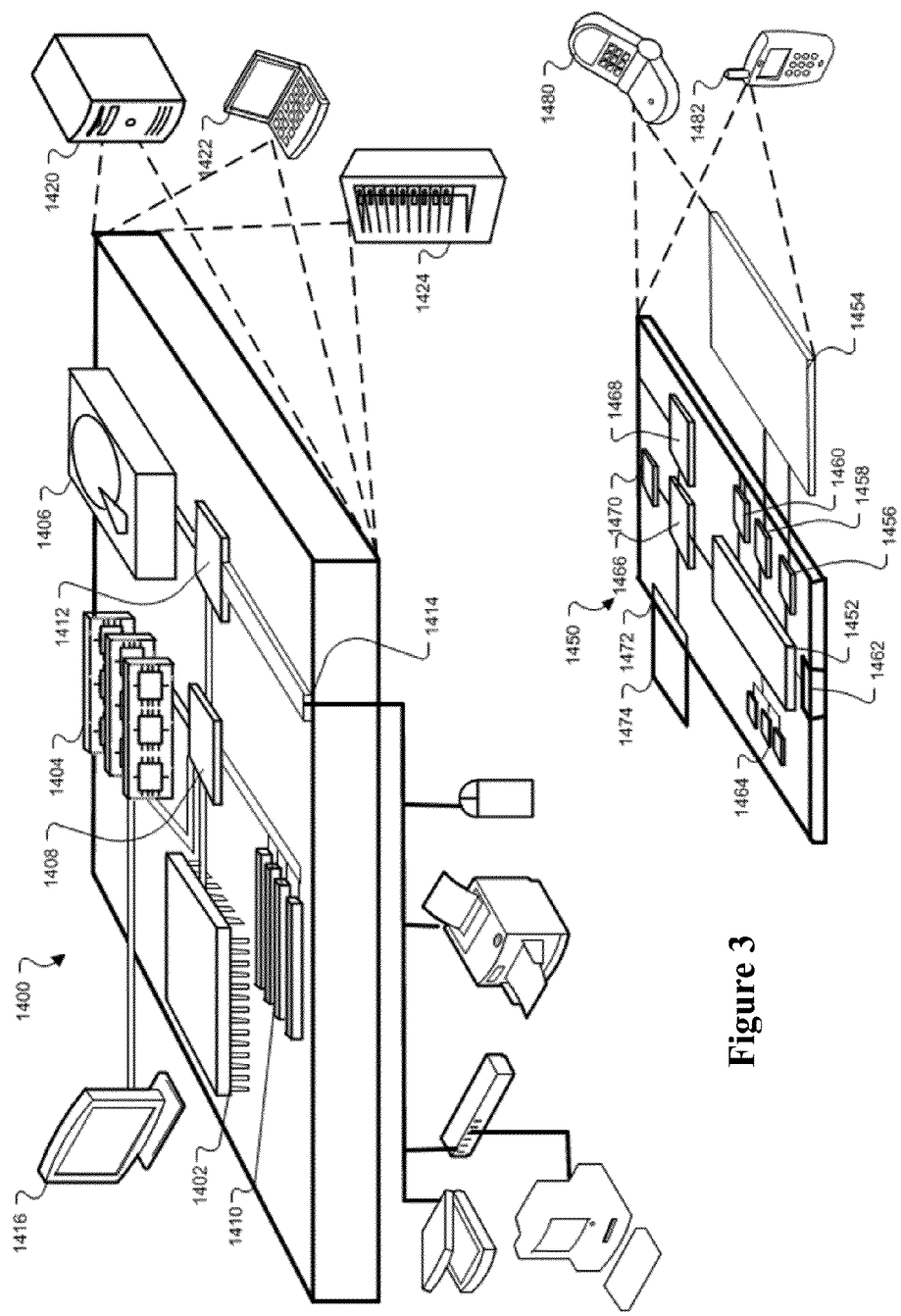
FIG. 3 is a diagram of an example of a generic computer device and a generic mobile computer device that can be used as described herein.

FIG. 3 is a diagram of an example of a generic computer device 1400 and a generic mobile computer device 1450, which may be used with the techniques described herein. Computing device 1400 is intended to represent various forms of digital computers, such as laptops, desktops, workstations, personal digital assistants, servers, blade servers, mainframes, and other appropriate computers. Computing device 1450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 1400 includes a processor 1402, memory 1404, a storage device 1406, a high-speed interface 1408 connecting to memory 1404 and high-speed expansion ports 1410, and a low speed interface 1415 connecting to low speed bus 1414 and storage device 1406. Each of the components 1402, 1404, 1406, 1408, 1410, and 1415, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described herein. The information carrier is a computer- or machine-readable medium, such as the memory 1404, the storage device 1406, memory on processor 1402, or a propagated signal.

The high speed controller 1408 manages bandwidth-intensive operations for the computing device 1400, while the low speed controller 1415 manages lower bandwidth-intensive operations. Such allocation of functions is exemplary only. In one implementation, the high-speed controller 1408 is coupled to memory 1404, display 1416 (e.g., through a graphics processor or accelerator), and to high-speed expansion ports 1410, which may accept various expansion cards (not shown). In the implementation, low-speed controller 1415 is coupled to storage device 1406 and low-speed expansion port 1414. The low-speed expansion port, which may include various communication ports (e.g., USB, Bluetooth, Ethernet, or wireless Ethernet) may be coupled to one or more input/output devices, such as a keyboard, a pointing device, a scanner, an optical reader, a fluorescent signal detector, or a networking device such as a switch or router, e.g., through a network adapter.

The computing device 1400 may be implemented in a number of different forms, as shown in the figure. For example, it may be implemented as a standard server 1420, or multiple times in a group of such servers. It may also be implemented as part of a rack server system 1424. In addition, it may be implemented in a personal computer such as a laptop computer 1422. In some cases, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components (e.g., a scanner, an optical reader, a fluorescent signal detector). The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT LCD (Thin-Film-Transistor Liquid Crystal Display) or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may be provide in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1474 may also be provided and connected to device 1450 through expansion interface 1472, which may include, for example, a SIMM (Single In Line Memory Module) card interface. Such expansion memory 1474 may provide extra storage space for device 1450, or may also store applications or other information for device 1450. For example, expansion memory 1474 may include instructions to carry out or supplement the processes described herein, and may include secure information also. Thus, for example, expansion memory 1474 may be provide as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described herein. The information carrier is a computer- or machine-readable medium, such as the memory 1464, expansion memory 1474, memory on processor 1452, or a propagated signal that may be received, for example, over transceiver 1468 or external interface 1462.

Device 1450 may communicate wirelessly through communication interface 1466, which may include digital signal processing circuitry where necessary. Communication interface 1466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1468. In addition, short-range communication may occur, such as using a Bluetooth, WiFi, or other such transceiver (not shown). In addition, GPS (Global Positioning System) receiver module 1470 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in the figure. For example, it may be implemented as a cellular telephone 1480. It may also be implemented as part of a smartphone 1482, personal digital assistant, or other similar mobile device.

Various implementations of the systems and techniques described herein can be realized in digital electronic circuitry, integrated circuitry, specially designed ASICs (application specific integrated circuits), computer hardware, firmware, software, and/or combinations thereof These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, and Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described herein can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described herein can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described herein), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

The invention will be further described in the following examples, which do not limit the scope of the invention described in the claims.

EXAMPLES

Example 1

Use of Clindamycin Pre-, Intra-, and Post-operatively

A patient scheduled to undergo a shoulder surgery (e.g., rotator cuff surgery or shoulder replacement surgery) is instructed to apply a cream containing clindamycin to the site of operation at least twice daily for 2-7 days prior to the day of surgery. Once in the patient is admitted to the hospital for the operation, a physician or other medical professional cleans the site of operation and applies a liquid formulation containing clindamycin. After the surgical wound is closed, a physician or other medical professional applies a formulation containing clindamycin to the site of operation. In some cases, a physician or other medical professional applies a patch or other material containing clindamycin to the site of operation. Prior to being discharged, the patient or the patient's caregiver is instructed to apply a formulation (e.g., cream) or a patch (or other material) containing clindamycin to the site of operation at least once daily for two to 14 days following surgery.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing risk of a post-operative *Propionibacterium acnes* infection following a shoulder surgery, wherein said method comprises:
   a) applying a first topical antibacterial composition to at least a portion of an operative site at least daily for two or more days before said shoulder surgery, and
   b) intra-operatively applying a surgical drape comprising a second topical antibacterial composition to at least a portion of the operative site,
   wherein the first and second topical antibacterial compositions comprise clindamycin, erythromycin, or a combination thereof.

2. The method of claim 1, wherein said shoulder surgery is selected from the group consisting of rotator cuff surgery, shoulder replacement surgery, instability surgery of the shoulder, clavicle fracture surgery, proximal humerus fracture surgery, and mid-shaft humerus fracture surgery.

3. The method of claim 1, wherein said first topical antibacterial composition is applied using a deodorant applicator.

4. The method of claim 1, wherein said first topical antibacterial composition is applied by wiping the skin with a wipe impregnated with said first topical antibacterial composition.

5. The method of claim 1, wherein said method further comprises dressing said surgical site post-operatively with dressings that are impregnated with a third topical antibacterial composition comprising clindamycin.

6. The method of claim 5, wherein first, second, or third topical antibacterial composition further comprises clindamycin or erythromycin and a second antibiotic.

* * * * *

UNITED STATES PATENT AND TRADEMARK OFFICE
CERTIFICATE OF CORRECTION

PATENT NO. : 9,176,487 B2  
APPLICATION NO. : 13/659607  
DATED : November 3, 2015  
INVENTOR(S) : John W. Sperling and Adam A. Sassoon Page 1 of 1

It is certified that error appears in the above-identified patent and that said Letters Patent is hereby corrected as shown below:

Title Page, Inventors, please delete "Adam A. Sassoon, Rochester, MN (US)" and insert -- Adam A. Sassoon, Orlando, FL (US) --;

Title Page, Related U.S. Application Data, please delete "Provisional application No. 61/550,795, filed on Oct. 24, 2011" and insert -- Provisional application No. 61/550,765, filed on Oct. 24, 2011 --; therefor.

Signed and Sealed this  
Twelfth Day of July, 2016

Michelle K. Lee  
*Director of the United States Patent and Trademark Office*